United States Patent [19]

Caspari et al.

[11] Patent Number: 4,616,637
[45] Date of Patent: Oct. 14, 1986

[54] SHOULDER TRACTION APPARATUS

[75] Inventors: Richard B. Caspari, Maidens; Terry L. Whipple; James A. Thimsen, both of Richmond, all of Va.

[73] Assignee: Precision Surgical Instruments, Inc., Richmond, Va.

[21] Appl. No.: 650,664

[22] Filed: Sep. 14, 1984

[51] Int. Cl.$^4$ ............................................. A61G 13/00
[52] U.S. Cl. .................... 128/84 R; 269/328; 128/84 B
[58] Field of Search ............... 128/84 R, 84 B, 84 C, 128/90, 75; 269/328

[56] References Cited

U.S. PATENT DOCUMENTS

| 1,257,764 | 2/1918 | Tascarella | 128/84 B |
| 2,306,929 | 12/1942 | Bergamini | 128/84 B |
| 2,590,739 | 3/1952 | Wagner et al. | 128/84 B |

Primary Examiner—F. Barry Shay
Attorney, Agent, or Firm—Richard P. Matthews

[57] ABSTRACT

A shoulder traction applying apparatus which clamps to an operating table. The forearm of a patient is gripped by a tapering sleeve-like member and a cord therefrom is entrained over a pair of pulleys at opposite ends of a boom member. The remote end of the cord is selectively weighted to apply tension to the cord and achieve a desired traction. The boom is secured to the top member of a pair of separable members of which the lower member is clamped to the operating table. The top member is rotatable by a hand crank which turns a worm gear that meshes with a spur gear fixedly secured to the top member. The lower member may be raised or lowered by cranking a pinion of a rack and pinion assembly wherein the rack is mounted on the lower member. Hand controlled spring pressure locks the lower member in the position selected by the rack and pinion assembly. A caster-mounted stand stores the top and lower members when the apparatus is not in use.

7 Claims, 11 Drawing Figures

SHOULDER TRACTION APPARATUS

This invention relates to traction applying apparatus and, more particularly, to a shoulder traction applying apparatus useful in shoulder arthroscopy with the apparatus being clamped to an operating table.

BACKGROUND OF THE INVENTION

Heretofore it has been common practice in performing shoulder arthroscopy to employ an assistant, unaided by any mechanical apparatus, to hold the arm of a patient in position for the duration of the operating procedure. It should be noted that shoulder arthroscopy involves complexities not encountered in knee arthroscopy. For example, in the former, the arm must simultaneously be elevated and distracted in a variety of configurations. A few mechanical devices have recently become available but they provide only unidirectional traction and are not structurally sound enough for a hospital environment.

SUMMARY OF THE INVENTION

In accordance with the present invention, the foregoing limitations and shortcomings of the known prior art are effectively overcome. In particular, a shoulder traction apparatus is provided that is not only rugged but also provides traction from any desired angle as well as from any desired elevation.

The forearm of the patient is gripped by a commercially available tapering pad to which a cord is attached. The cord is strung across a pair of pulleys on a boom means whereby the supporting structure for the boom means is positioned unobtrusively out of the surgical field. The remote end of the cord receives standard traction weights placing the cord under tension and supplying the desired amount of traction.

The supporting structure for the boom includes a lower portion which clamps to a conventional rail of the operating table. This lower portion includes a hand crank-operated rack and pinion assembly whereby multi-elevational positions may be obtained for the boom by raising or lowering a rectangular or square hollow tube to which the rack is attached. Frictional spring clamping means are also provided to prevent change in elevation when a desired position is set.

The supporting structure for the boom also includes an upper portion which partially telescopes into the lower portion. This upper portion carries the boom itself and provides means for rotating the boom, such as a worm gear and spur gear combination, about a vertical axis.

Finally, the entire assembly of upper and lower supporting structures may be separated and stored in an out-of-the-way location by means of a rugged storage cart. The cart is mounted on casters and is provided with hollow tubular members into which the upper and lower supporting structures may be inserted.

The inherent advantages and improvements of the present invention will become more apparent by reference to the following detailed description of the invention and by reference to the drawings wherein.

DETAILED DESCRIPTION OF THE INVENTION

Figure 1:
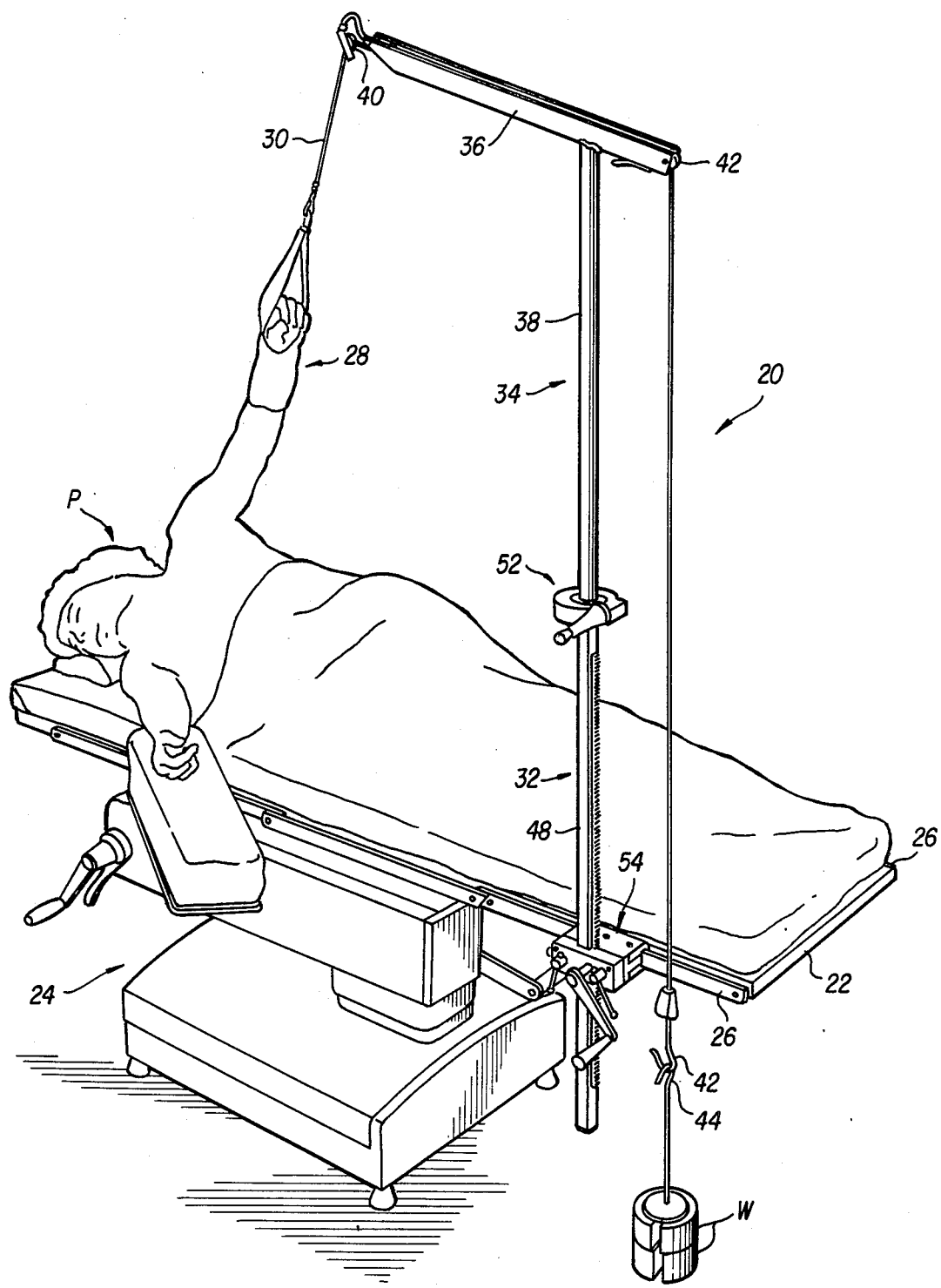
FIG. 1 is a perspective view illustrating the use of the present invention.

Referring now to FIG. 1 in the drawings, there is indicated a traction applying apparatus indicated generally at 20 in which a patient P is shown lying on an operating table 22. The operating table is supported by a suitable stand or support indicated generally at 24. The table is equipped with a pair of guard rails 26 on opposite sides of the table with the guard rails being conventional. The forearm of the arm to be operated upon is encased within a tapering sheath or gripping means indicated generally at 28 with the gripping means being conventionally available and shown in greater detail in FIG. 10.

A cord 30 is secured to this gripping means 28 and is threaded over boom means which includes a first or lower portion, indicated generally at 32, and a second or upper portion 34. A boom member 36 is fixedly secured such as by welding to the upper end of a hollow cylindrical tube member 38 of the upper portion 34. Cord 30 is threaded over pulleys 40, 42 at opposite ends of the boom member 36 and a hook member 44 is secured at the lower end of the cord. Hook member 44 supports another hook member 46 which carries a series of selectively applied weights W in order to place cord 30 under tension and achieve a desired traction for the arm of the patient.

Figure 2:
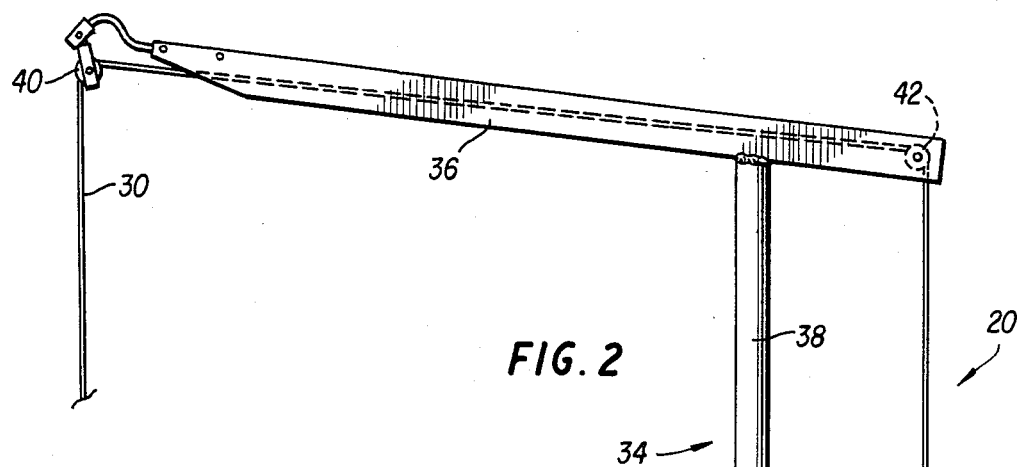
FIG. 2 is an exploded view of the major components of FIG. 1, taken partially in vertical cross section.
Figure 3:
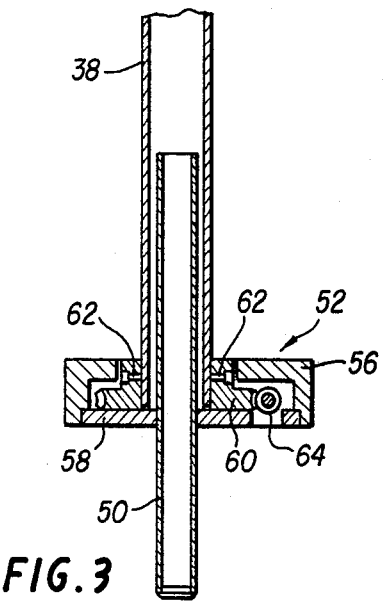
FIG. 3 is a fragmentary elevational view taken in vertical cross section along line 3—3 of FIG. 4.
Figure 4:
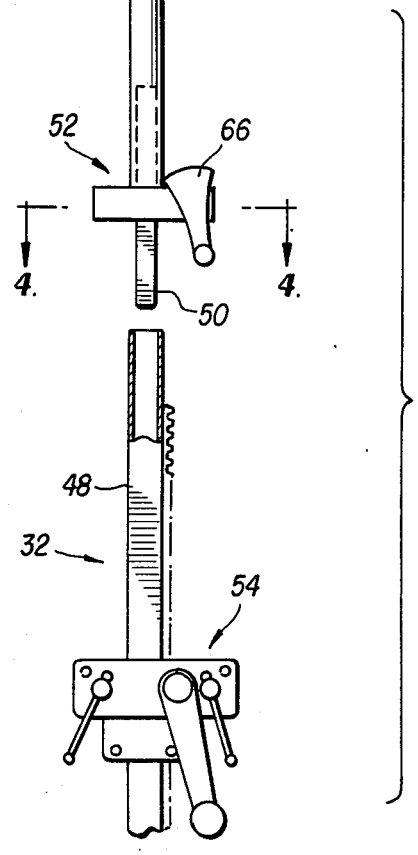
FIG. 4 is a plan view taken in horizontal cross section along line 4—4 of FIG. 2 and drawn to an enlarged scale.
Figure 4:
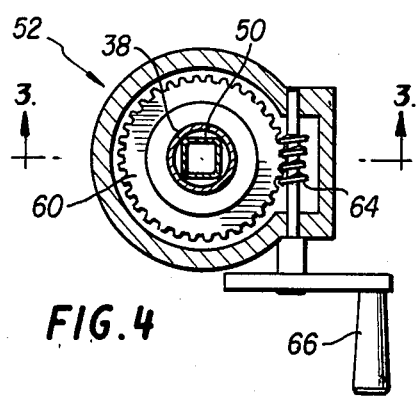
Figure 5:
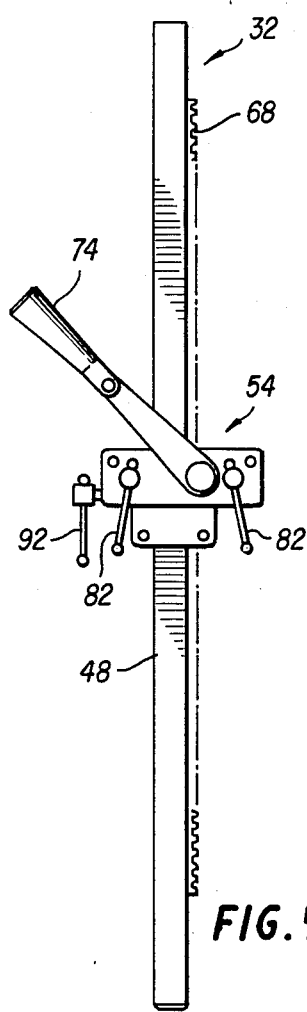
FIG. 5 is a front elevational view of the lower portion of the apparatus of FIG. 1.
Figure 6:
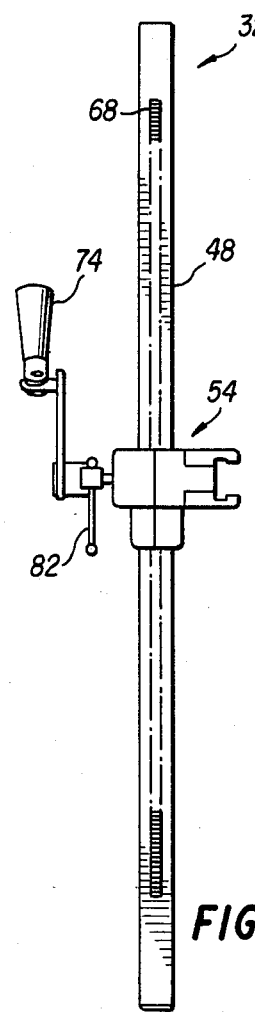
FIG. 6 is a side elevational view of the apparatus shown in FIG. 5.

As is illustrated in FIGS. 2-4, the hollow tube member 38 is provided at its lower extremity with an interconnecting or splicing tube member 50 which, as is seen in FIG. 4, is either square or rectangular in cross section and it is frictionally received within bottom 58 of housing 52. Hollow tube member 38 has an inner diameter sufficiently large to permit its rotation and thereby rotation of the attached boom member 36 about a vertical axis. The means for imparting the rotation to hollow member 38 is contained within a housing indicated generally at 52. FIG. 2 also shows a housing 54 containing the means for raising and lowering boom member 36 which will be described hereinafter.

Referring now to FIGS. 3 and 4, there is illustrated a preferred means for rotating the boom member 36. Housing 52 is shown to have a top member 56 with depending side skirts with the housing enclosure being completed by bottom member 58. A spur gear 60 is attached to the lower end of hollow tube member 38 and the spur gear 60 is secured by securing means 62 which can take the form of pins or set screw means. Spur gear 60 is in mesh with a worm gear 64 and a suitable crank handle 66 provides means to turn the worm gear 64 which concurrently turns the spur gear 60 and thereby rotates hollow tube member 38 and its attached boom member 36. Therefore, it is possible to provide multidirectional, substantially infinitely variable, traction for the patient's arm.

Figure 7:
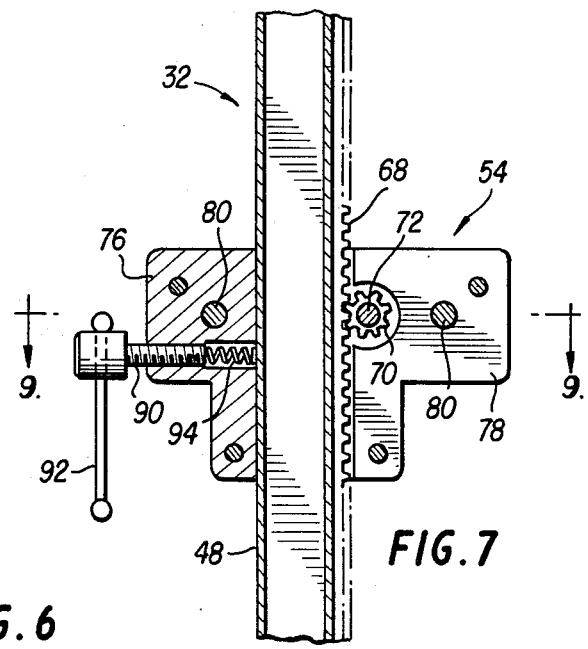
FIG. 7 is a fragmentary elevational view taken in vertical cross section along line 7—7 of FIG. 9.
Figure 8:
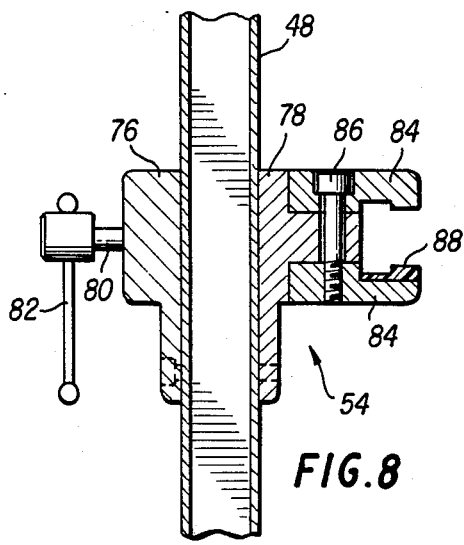
FIG. 8 is a fragmentary elevational view taken in vertical cross section along line 8—8 of FIG. 9.
Figure 9:
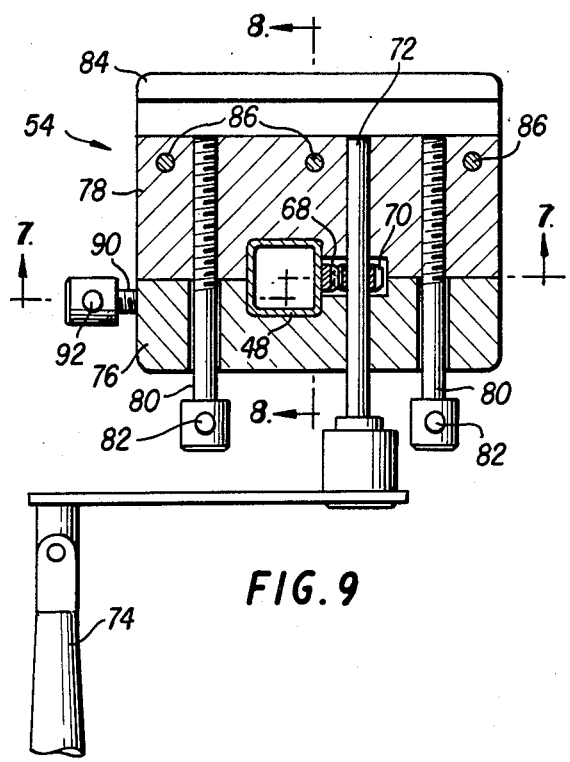
FIG. 9 is a plan view taken in horizontal cross section along line 9—9 of FIG. 7.

FIGS. 5-9 illustrate the means for raising and lowering the lower portion 32 of the boom means. A rack 68 is attached externally of the hollow tube member 48 which as is shown in FIG. 9 is either rectangular or square in cross section. A pinion 70, as seen in FIGS. 7 and 9, meshes with rack 68 and is mounted on shaft 72 which is rotated by a hand crank mechanism 74. Housing 54 is shown to have a rear portion 76 and a front portion 78. A pair of bolt means 80 are individually controlled by a handle 82 in a suitable position so that hollow tube member 48 may be contained by housing 54.

A pair of guard rail clamping jaws 84 are secured to the front portion 78 of housing 54 by a series of laterally spaced bolts 86. As an optional feature, a plastic gripping element 88 may be inserted within the jaws 84 for engagement with the guard rail 26.

As is illustrated best in FIG. 7, after the assembled boom means has been positioned in the desired elevation by means of rotating the hand crank mechanism 74, a bolt member 90 is turned by handle 92 in order to make compression spring 94 engage the outside of the hollow tube member 48 and thereby clamp the boom means in its desired elevational position.

Figure 10:
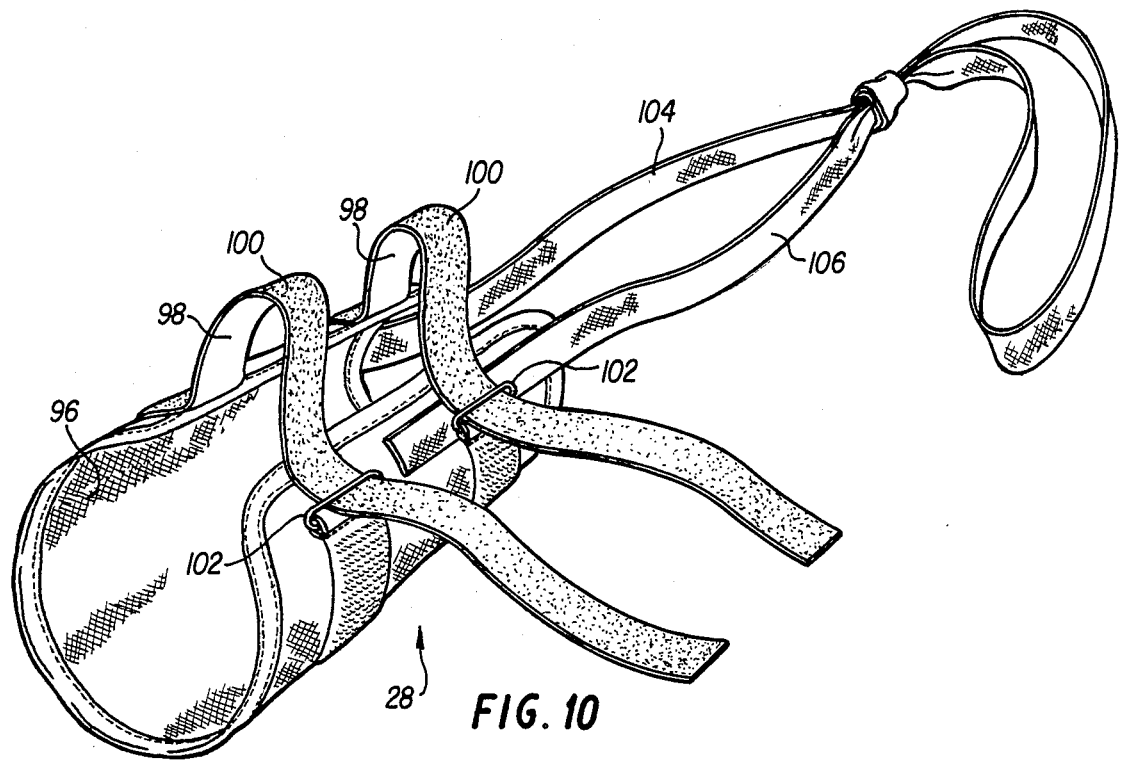
FIG. 10 is a perspective view of a forearm gripping device.

The forearm engaging tapering sheath includes an inner portion 96 which may be lined with rubber, Neoprene or the like, and is shown in FIG. 10. This sheath further includes a pair of straps 98 which are provided with Velcro attaching means 100 on one side thereof. Velcro is a trademark of Velcro, Inc., of Manchester, N.H. for separable fasteners, namely, hook and loop type fasteners. After the straps 98 are slipped through metal loops 102 they are folded back upon themselves with the mating Velcro portions providing securement. Straps 104, 106 are shown parallel to the longitudinal edges of the sheath and the loops are shown to be knotted to provide a loop at the end for securement of the traction applying cord 30.

Figure 11:
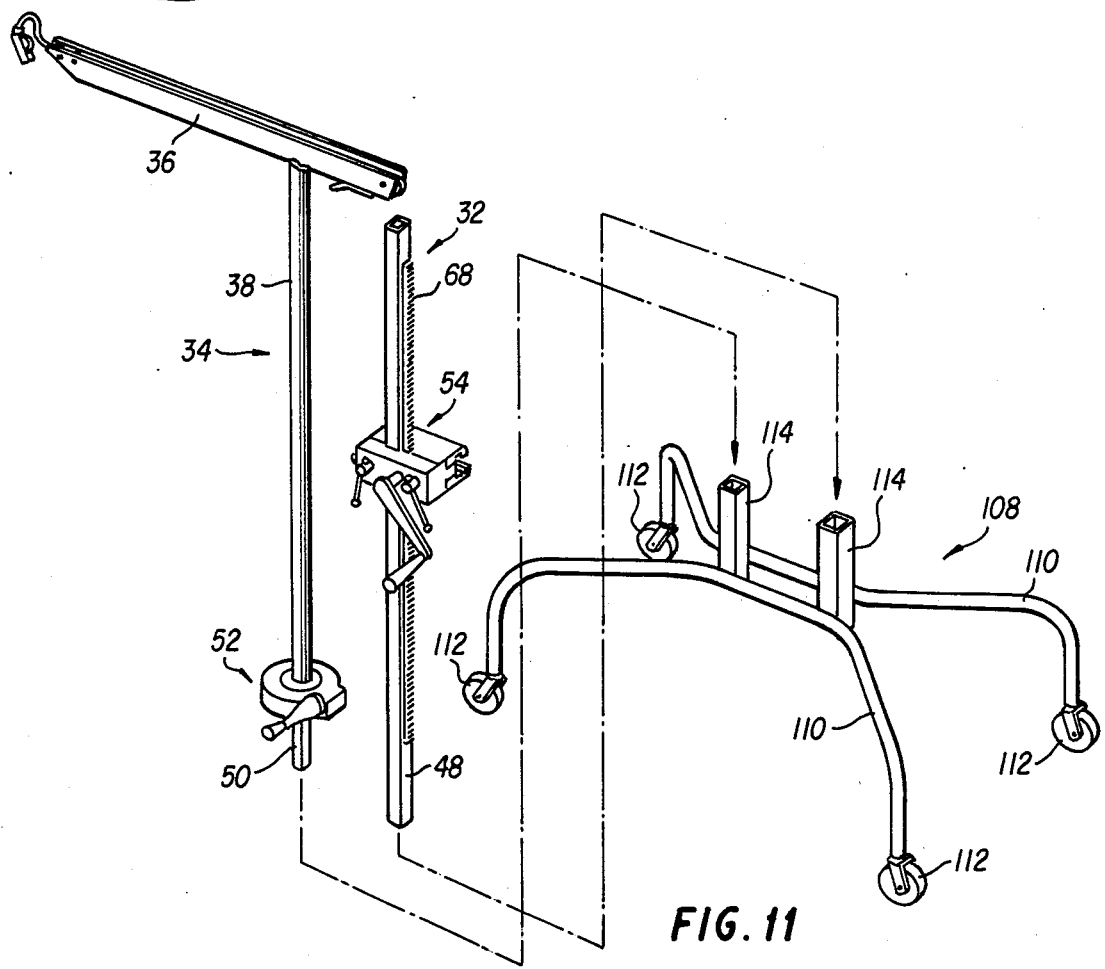
FIG. 11 is an exploded perspective view of a storage cart adapted to receive the two principal portions of the traction applying apparatus.

FIG. 11 illustrates a suitable stand 108 for the two portions 32, 34 of the boom means. Stand 108 is shown to be provided with a pair of bent frame members 110 mounted on casters 112 and provided with a pair of hollow rectangular tubes 114 into which the square or rectangular members 48, 50 are inserted. Therefore, the entire assembly of the upper and lower supporting structures may be stored in an out-of-the-way location.

The shoulder traction applying apparatus of the present invention is extremely versatile and can be used for other procedures in the operating room which include the preparation for shoulder cases, setting Colles fractures, reducing humeral fractures, and reducing or pinning many fractures of the upper extremity of a patient's body. The apparatus has proved to be quite beneficial to arthroscopic surgery. It facilitates precise, efficient and rapid shoulder arthroscopy and simplifies arthroscopic shoulder surgery for all members of the surgical team. As is illustrated especially in FIG. 1 of the drawings, the length of the boom 36 is such that the apparatus used to effect the desired traction may be clamped to the operating bed at a position substantially removed from the upper body portion of the patient P whereby the surgeon is provided with an unobstructed view of the surgical field.

While the invention has been illustrated and described with respect to a preferred embodiment thereof, it will be understood that the invention may be otherwise variously embodied and practiced without departing from the scope of the claims which follow.

We claim:

1. In a shoulder traction applying apparatus, the combination which comprises
    a. boom means secured to an operating table,
       (1) said boom means having an upper rotatable portion which extends above and is rotatable relative to said operating table and a lower non-rotatable portion which is fixed relative to said table,
    b. means secured to said lower non-rotatable portion for varying the elevation of said boom means,
    c. a boom member carried by said upper rotatable portion of said boom means,
    d. cord means carried by said boom member and being advanceable forwardly and rearwardly along said boom member,
    e. gripping means attached to a forward end of said cord means with said gripping means gripping the arm of the patient,
    f. variable means connected to a rearward end of said cord means for applying tension to said cord means whereby said tension will not increase because of movement of the patient,
    g. and gear means carried by said rotatable portion for co-action with means on said non-rotatable portion for rotating said rotatable portion of said boom means about a vertical axis.

2. A shoulder traction applying apparatus as defined in claim 1 wherein said upper rotatable portion of said boom means comprises a circular tube member having a spur gear secured thereto.

3. A shoulder traction applying apparatus as defined in claim 1 wherein said upper rotatable portion of said boom means further includes worm gear means meshing with said spur gear and means to turn said worm gear means.

4. A shoulder traction applying apparatus as defined in claim 1 including means carried by said lower non-rotatable portion of said boom means to vary the elevation of said boom means.

5. A shoulder traction applying apparatus as defined in claim 4 wherein said means to vary the elevation of said boom means comprises a rack and pinion assembly with means to rotate said pinion.

6. A shoulder traction applying apparatus as defined in claim 5 wherein said non-rotatable portion of said boom means is provided with a hollow tubular member of rectangular cross section and said rack is carried by said hollow tubular member externally thereof.

7. A shoulder traction applying apparatus as defined in claim 6 wherein said first non-rotatable portion of said boom means is provided with adjustable spring pressure means to hold said hollow tubular member of rectangular cross section in a fixed position as selected by said rack and pinion assembly.

* * * * *